Oct. 2, 1956 G. J. VON ABRAMS Plant Pat. 1,523
ROSE PLANT
Filed Nov. 2, 1955
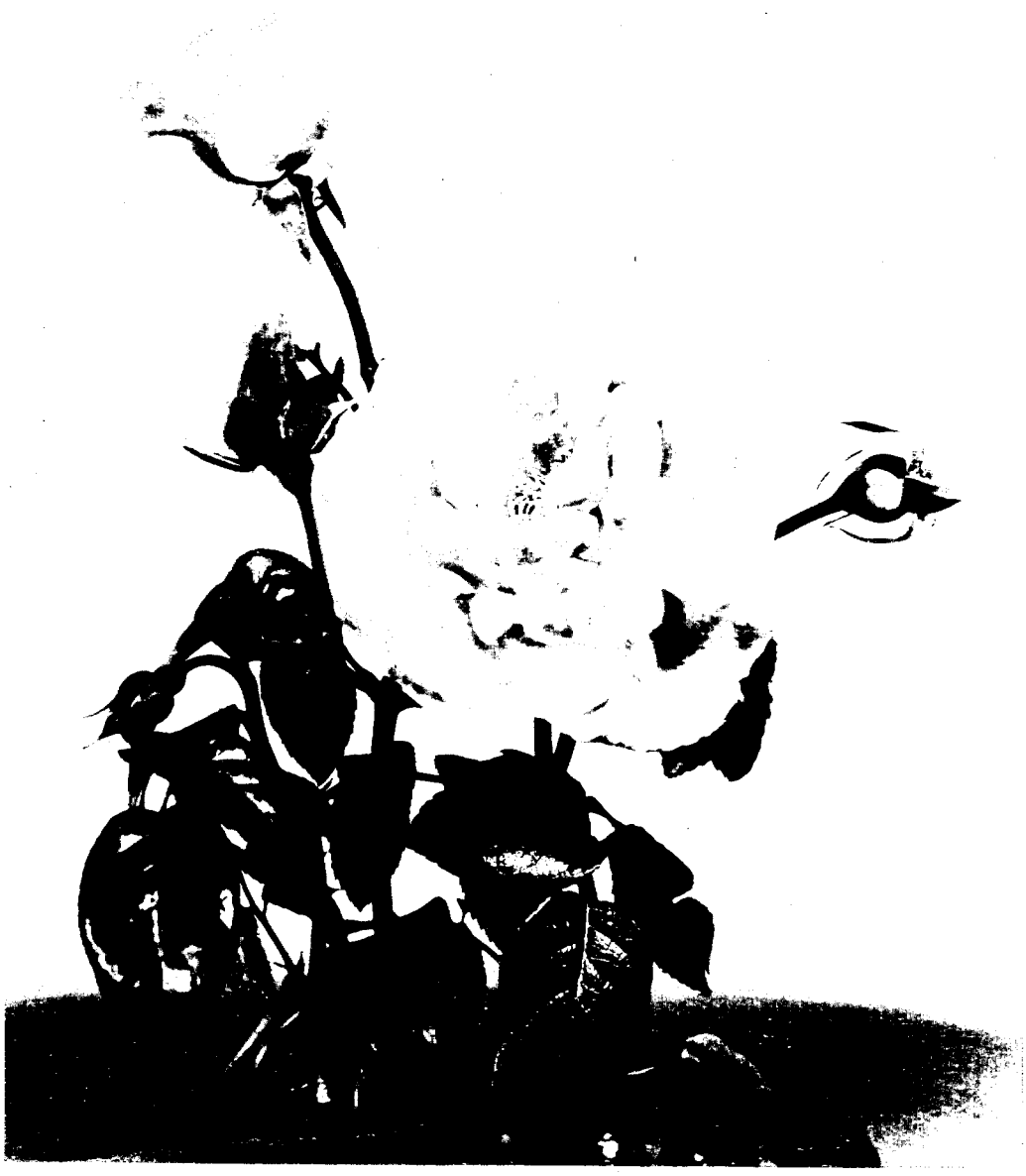
Inventor.
G. J. Von Abrams
By: Robb & Robb
Attorneys.

United States Patent Office

Plant Pat. 1,523
Patented Oct. 2, 1956

1,523

ROSE PLANT

Gordon J. Von Abrams, Scappoose, Oreg., assignor to Eldon Pinkeney Dering, doing business under the name of Peterson & Dering, Scappoose, Oreg.

Application November 2, 1955, Serial No. 544,626

1 Claim. (Cl. 47—61)

The present invention relates to a new and distinct variety of rose plant of the hybrid tea class, which was originated by me by crossing the variety "Juno" (Plant Patent No. 895) with an unnamed and unpatented seedling derived from a cross of "Georg Arends" (unpatented) X "New Dawn" (Plant Patent No. 1), said latter seedling being identified in my breeding records as #49361.

The primary objective of this breeding was to produce a new rose variety in which the glossy texture of the foliage is intensified and which is endowed with an increased general hardiness of the plant without appreciable effect upon the conventionally desired form of its flowers. This objective has been fully achieved, as evidenced by the following predominant features which phenotypically characterize the new variety:

(1) The upright, bushy, vigorous and moderately tall (up to 4 feet) habit of growth of the plant;

(2) The extremely glossy foliage which is very bright in color, plentiful, well-distributed and large in size, said bright color and the clean and orderly appearance, in combination with the other features, particularly and readily distinguishing and identifying the new variety;

(3) Improved disease resistance and cold tolerance which are above average of the class;

(4) Continuous and prolific flowering habit throughout the growing season, with the flowers sometimes borne singly, but usually in small cymes; and (5) A unique combination of form and color of the flowers which is distinct from any other rose in commerce of which I am aware.

In comparison with its seed parent, "Juno," the plant of my new variety is more vigorous and upright in habit; the upper surface of the foliage is more smooth and glossy, its color lighter and brighter, particularly before maturity, lighter in substance and less brittle, with the stipules larger and having more distinct points; the flowers are more slender and elongate, with fewer petals and being slightly lighter in color; much more prolific in flowering habit; and the general hardiness is substantially improved, as evidenced by greater cold tolerance and greater disease resistance.

As compared with its pollen parent, the plant of the new variety is less vigorous, but of better proportion and symmetry; the foliage is larger and heavier in substance; and the flowers are larger, more slender and elongate, with fewer petals and a more refined mature form.

Asexual reproduction of the new variety by bud-grafting, as performed by me at Scappoose, Oregon, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Hardy; upright bush; outdoor; for cut flowers and for garden decoration.

Class: Hybrid tea.

Parentage:

*Seed Parent.*—"Juno."

*Pollen Parent.*—An unnamed seedling derived from "Georg Arends" X "New Dawn."

Propagation: Holds it distinguishing characteristics through succeeding propagations by bud-grafting.

FLOWER

Locality where grown and observed: Scappoose, Oregon.

Flowers borne: Sometimes singly, but usually in small cymes numbering up to 10 per stem; on strong, moderately long stems.

Quantity of bloom: Abundant, outdoors.

Continuity: Continuous during the growing season.

Fragrance: From slight to moderate. Nature—spicy.

Bud:

*Peduncle.*—Medium length (from 6 to 8 cm.); heavy; erect; usually smooth and glossy; with few fine glandular cilia. Color—Light Green, flushed with Red.

*Before calyx breaks.*—Size—medium (about 2.5 x 1.8 cm., excluding receptacle). Form—pointed; with conspicuous neck; without foliaceous appendages on the surface of the bud; long (up to 7 mm.), slender foliaceous appendages occur on the lateral margins of most sepals, but in no apparent order and may vary in number from none to 6 per sepal; usually with slightly serrate foliaceous parts extending beyond the tip of the bud less than 1/4 of its length. Color—near Lettuce Green, Plate V, 29.k (Ridgway), slightly flushed with Maroon.

*As calyx breaks.*—Color—Pomegranate Purple, Plate XII, 71.i (Ridgway) or darker.

*As first petal opens.*—Size—from medium to large (from 4.5 to 6 cm. long). Form—from long-pointed to urn-shaped. Color: outside—Crimson, Plate 22, page 22 (Wilson) near base, flushing upward to Rose Madder, Plate 23/1, page 23 (Wilson) or Plate 23/2, page 23 (Wilson), with small basal spot of Pinard Yellow, Plate IV, 21.d (Ridgway); inside—Carmine, Plate 21, page 21 (Wilson) near base, flushing upward along veins into from Tyrian Rose, Plate 24/1, page 24 (Wilson) to Tyrian Rose, Plate 24/2, page 24 (Wilson), with large basal spot of Lemon Yellow, Plate 4, page 4 (Wilson), flushing upward.

*Opening.*—Opens up very well under all reasonable climatic conditions.

Bloom:

*Size (when fully open).*—From medium to large (from 9 to 15 cm.).

*Petalage.*—Double; from 21 to 28 petals; arranged regularly.

*Form.*—High-centered at first, but becoming cupped and remaining loosely cupped to maturity; loosely cupped petals have slight outward roll at upper edges.

Petals:

*Texture.*—Medium thickness; slightly soft. Inner surface—velvety. Outer surface—satiny.

*Shape.*—Outer petal—Rotund; very broad (5.5 cm. long x 6 cm. wide); apex sometimes mucronate.

Intermediate petal—broad obovate, with apex from entire to irregular. Inner petal—obovate (5.5 x 4.5 cm.); apex irregular; slight irregular crenation along apical edge.

This description of a newly opened flower was made from a rose grown outdoors in the month of August, at Scappoose, Oregon:

*Color.*—Outer petal: outside surface—from Rose Madder, Plate 23/1, page 23 (Wilson) to Rose Madder, Plate 23/2, page 23 (Wilson), flushed near base with Carmine, Plate 21, page 21 (Wilson), but lighter near margins and fading sharply to a narrow (less than 1 mm.) White or near-white border, with basal spot of Pinard Yellow, Plate IV, 21.d (Ridgway); inside surface—Tyrian Rose, Plate 24/2, page 24 (Wilson), flushed near base with Carmine, Plate 21, page 21 (Wilson), but lighter towards margins, with basal spot of Lemon Yellow, Plate 4, page 4 (Wilson). Intermediate petal: outside surface—from Rose Madder, Plate 23/2, page 23 (Wilson) to Crimson, Plate 22/2, page 22 (Wilson), but lighter towards margins, with narrow (less than 0.5 mm.) near-white border and slight Carmine, Plate 21/1, page 21 (Wilson) flush near base, and with small basal spot near Sulphur Yellow, Plate 1/2, page 1 (Wilson); inside surface—from Crimson, Plate 22/2, page 22 (Wilson) to Crimson, Plate 22/1, page 22 (Wilson), but lighter towards margins, with very narrow near-white border and Carmine, Plate 21, page 21 (Wilson) flush near base, and with basal spot of Lemon Yellow, Plate 4, page 4 (Wilson). Inner petal: outside surface—Crimson, Plate 22/1, page 22 (Wilson), but lighter toward margins, with a very narrow near-white border, and with small basal spot of Sulphur Yellow, Plate 1/2, page 1 (Wilson); inside surface—from Carmine, Plate 21/1, page 21 (Wilson) near base to Crimson, Plate 22/1, page 22 (Wilson) or lighter toward margins, with a very narrow near-white border, and with basal spot of Lemon Yellow, Plate 4, page 4 (Wilson). General color effect—tints of from Neyron Rose, Plate 623, page 76 (Wilson) to Neyron Rose, Plate 623/3, page 76 (Wilson).

This description was made from a rose that was open for 3 days outdoors in the month of August, at Scappoose, Oregon:

*Color.*—Outer petal: outside surface—Tyrian Rose, Plate 24/2, page 24 (Wilson), penciled with Tyrian Rose, Plate 24/1, page 24 (Wilson), and lightly flushed with Tyrian Rose, Plate 24/3, page 24 (Wilson) at apex and near base, with small basal spot of Empire Yellow, Plate IV, 21.b (Ridgway); inside surface—Tyrian Rose, Plate 24/3, page 24 (Wilson), with veins of slightly darker Tyrian Rose, Plate 24/2, page 24 (Wilson), and with basal spot of Pinard Yellow, Plate IV, 21.d (Ridgway), merging into near-white. Inner petal: outside surface—between Tyrian Rose, Plate 24/2, page 24 (Wilson) and Tyrian Rose, Plate 24/3, page 24 (Wilson), with small basal spot of Empire Yellow, Plate IV, 21.b (Ridgway); inside surface—near Crimson, Plate 22/3, page 22 (Wilson), with some lighter flush, particularly along basal lateral margins. General color effect—Rose Madder, Plate 23/3, page 23 (Wilson), with darker shading of Rose Madder, Plate 23/2, page 23 (Wilson).

*Behavior.*—Petals drop off cleanly; fade gradually to lighter color; blooms are geenrally smaller during extended periods of hot, dry weather, and petals show a flush of light Tan color.

*Flower longevity.*—On bush in garden—4 days in August. Cut roses grown outdoors and kept at living-room temperatures—3 days in August.

REPRODUCTIVE ORGANS

Stamens: Many; arranged regularly about pistils on margin of receptacle.

Filaments: From medium length to long (up to 1.5 cm.); most all with anthers. Color—Orange, flushed with Maroon.

Anthers: Medium size (about 1.5 x 4 mm.); open over short period of time.

Pollen: Moderately abundant. Color—variable Dark Gold.

Pistils: Many.

Styles: Quite even; shorter in center of column; medium length (about 1 cm.); medium caliper; closely bunched.

Stigma: Moderate size. Color—Pale Buff.

Ovaries: All enclosed in receptacle.

Fruit: Large (about 2.7 x 2.5 cm.); from obovoid to broad-turbinate; smooth; walls moderately thick (about 3 mm.) and fleshy. Color—from Orange to Red, depending upon environment during development and at maturity.

Sepals: Persistent; long (about 3.2 cm.); spear-shaped; neither curled nor recurved; nearly upright. Color—variable from Spinach Green, Plate V, 29.m (Ridgway) to Lettuce Green, Plate V, 29.k (Ridgway), flushed with Maroon.

Seeds: Many; medium size.

PLANT

Foliage:

*Leaves.*—Compound of 3 to 7, but usually 5 leaflets; abundant; medium large; medium heavy; leathery; extremely glossy.

*Leaflets.*—Shape—ovate, with apex from acute to slightly mucronate. Base—sometimes slightly cordate. Margin—simply serrate. Size—to about 5.5 x 9.5 cm.

*Color.*—Mature: upper surface—near Forest Green, Plate XVII, 29'.m (Ridgway); under surface—near Biscay Green, Plate XVII, 27'.i (Ridgway). Young; upper surface—from near Scheeles Green, Plate 860, page 175 (Wilson) to Scheeles Green, Plate 860/2, page 175 (Wilson), or darker, with mid-rib and margins Maroon; under surface—near Biscay Green, Plate XVII, 27'.i (Ridgway), flushed Maroon, and with mid-rib, main veins and margins of Maroon.

*Rachis (the supporting stem of the compound leaf).*—Heavy. Upper surface—grooved; with several glandular cilia on margins; under surface—Sparsely thorny, with few glandular cilia.

*Stipules.*—Medium size (about 2 x 1 cm.); with medium long points usually turning out at an angle of less than 45°; margins finely serrate.

*Disease resistance and cold tolerance.*—Well above average resistance to mildew, rust and blackspot, and greater cold tolerance as determined from comparison with other varieties of the same class grown under comparable cultural conditions at Scappoose, Oregon.

Growth:

*Habit.*—Upright; bushy; well-branched; symmetrical.

*Growth.*—Vigorous.

*Canes.*—Medium heavy.

*Main Stems.*—Color—from Bright Green to Grey-Green where corky. Thorns—several; medium length; hooked slightly downward; with long, oval base. Prickles — few. Color — Gray. Hairs—none.

*Branches.*—Color—Bronzy Green. Thorns—several; medium length; hooked downward slightly. Prickles—few. Color—reddish. Cilia—several. Color—reddish.

*New Shoots.*—Color—variable reddish. Thorns—several; hooked slightly downward; with long, oval base. Color—Red. Prickles—few. Color—Red. Cilia—several; glandular. Color—Red.

I claim:

A new and distinct variety of rose plant of the hybrid tea class, substantially as herein shown and described, characterized particularly as to novelty by its upright, bushy, vigorous and moderately tall habit of growth, its plentiful, well-distributed, large, extremely glossy and very brilliant foliage which presents a clean and orderly appearance, its above-average disease resistance and cold tolerance, its continuous and prolific flowering habit throughout the growing season, with the flowers borne sometimes singly, but usually in small cymes, and the unique combination of form and distinctive color of its flowers.

No references cited.